United States Patent [19]

Fluri et al.

[11] 4,256,837
[45] Mar. 17, 1981

[54] GAS COLLECTION APPARATUS

[75] Inventors: Peter Fluri, Domat; Richard Voser, Chur; Peter Wettstein, Domat, all of Switzerland

[73] Assignee: Inventa AG für Forschung und Patentverwertung, Zurich, Zurich, Switzerland

[21] Appl. No.: 91,023

[22] Filed: Nov. 5, 1979

[30] Foreign Application Priority Data

Nov. 6, 1978 [CH] Switzerland .................. 11382/78
Jul. 5, 1979 [CH] Switzerland .................... 6288/79

[51] Int. Cl.³ .............................................. C12P 5/02
[52] U.S. Cl. .................................... 435/167; 210/188;
210/DIG. 9; 210/608; 435/287; 435/316;
435/801; 435/812
[58] Field of Search ........... 210/13, 170, 188, DIG. 9;
48/111, 197 A; 422/184; 435/287, 316, 801,
812, 167

[56] References Cited

U.S. PATENT DOCUMENTS

| 2,202,772 | 5/1940 | Durdin, Jr. | 210/DIG. 9 |
| 2,422,394 | 6/1947 | Carter, Jr. | 210/DIG. 9 |
| 3,187,897 | 6/1965 | Walker | 210/DIG. 9 |
| 4,166,835 | 9/1979 | Anderson | 422/184 |

Primary Examiner—Robert J. Warden
Attorney, Agent, or Firm—Bierman & Bierman

[57] ABSTRACT

An apparatus and method for the recovery of gas evolved from fermentation is disclosed. The apparatus comprises a vessel containing the fermentation material, and a head slidably mounted on the vessel forming a substantially gas tight chamber therewith. Mounted on the head are a series of projections of various shapes which extend into the chamber. As the fermentation proceeds, the generation of gas causes the head to rise. When it has risen a sufficient amount, a gas outlet valve is opened and the gas is introduced into a collector. The reduction in gas pressure causes the head to drop. The movement of the head causes the projections to break through the scum layer at the surface of the fermentation broth, thereby enhancing the reaction. In a preferred form of the device, the projections are so formed as to urge the scum towards the discharge means, thereby breaking and removing the scum without the use of any additional energy. A method for using the apparatus is also disclosed.

14 Claims, 3 Drawing Figures

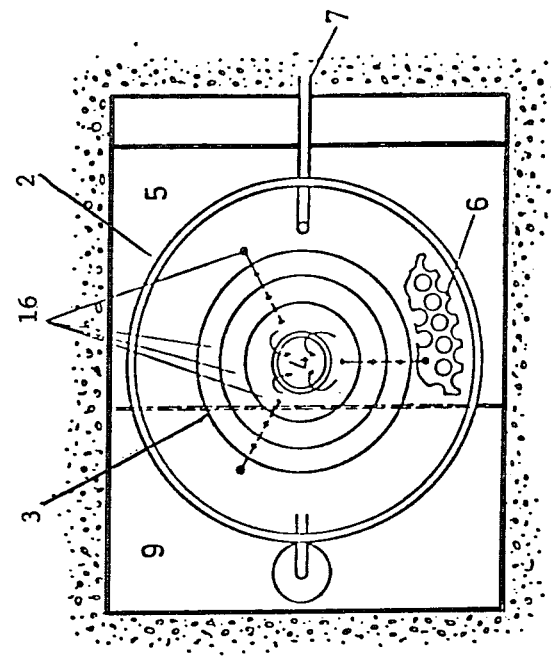
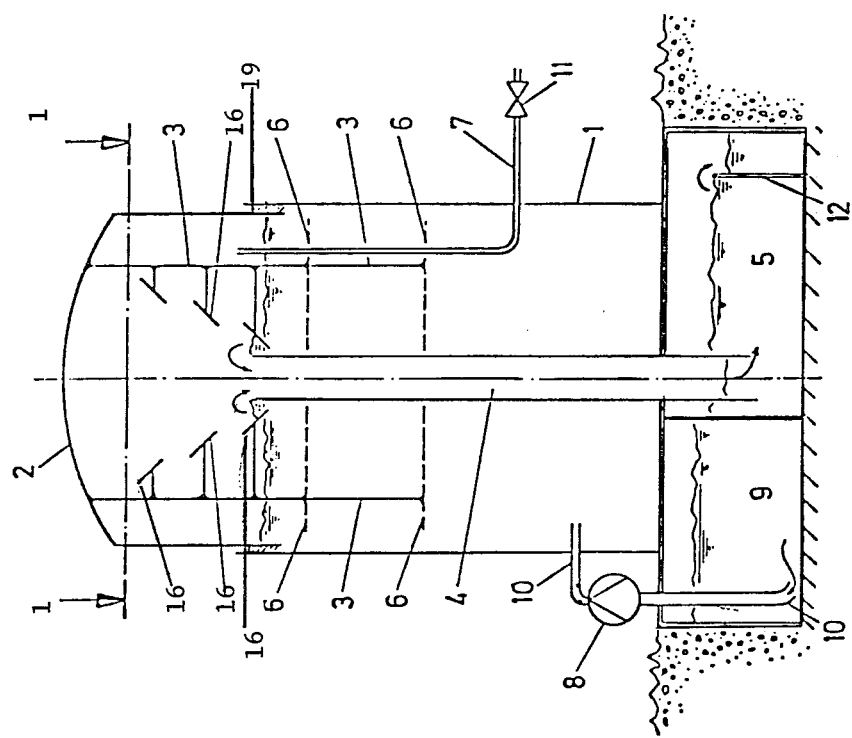

GAS COLLECTION APPARATUS

This application claims the priority of Swiss Patent Application No. 11 382/78 filed Nov. 6th, 1978 and Swiss Patent Application No. 6 288/79 filed July 5th, 1979.

The present invention is directed to an apparatus and method for use in collecting gas obtained during fermentation. It is particularly adapted for use in the anaerobic fermentation of liquid wastes; especially animal and plant wastes. It is particularly useful in the treatment of liquid manure by methane-producing bacteria.

Such bacteria usually produce a gas which is approximately two thirds methane and one third carbon dioxide. Such gas has a high heat value and is of great interest in these times of increasing energy costs and diminishing supply. This gas is readily obtained from generally available materials.

Moreover, after fermentation is complete, the waste materials are not especially foul smelling and, for this reason, can be more conveniently used for agricultural fertilizer.

For ecological reasons, there has been increased interest in the use of natural fertilizers (such as fermented manure) in all forms of agriculture. Heretofore, such fermentation has been carried out in insulated heated containers which are provided with a pump to supply the waste.

However, the raw waste usually comes with various forms of plant matter, such as hay, straw, grass, etc. It has not been found feasible to separate or otherwise deal with this material. It forms a scum layer on the surface of the fermenting broth and should be broken up and/or removed in order to facilitate the fermentation reaction.

For this reason, prior fermenting devices have included means for stirring the waste and breaking up the scum, which means usually comprises some form of powered agitator.

In fact, the problem is so severe, that attempts have been made to avoid it by not using straw or grass in animal stalls, by chopping up the straw or grass, by comminuting the manure prior to fermentation, removing the scum from the waste prior to fermentation, centrifuging, etc. All of these measures are inefficient insofar as cost, energy and maintenance are concerned. It is frequently necessary to interrupt the process in order to remove the scum.

In accordance with the present invention, it has now been found that it is possible to use the gas which is naturally evolved from the fermentation reaction to provide the necessary energy to break up the undesired scum and remove it from the reation vessel. This can be done without interrupting the introduction of the waste, the removal of the fermented waste, and the evolution of the desired gas.

In accordance with the present invention, there is provided a vessel which is adapted to receive the fermentable material. A head is mounted on the vessel and is movable toward and away from it. The vessel and head together form a chamber which is substantially gas tight.

Means is also provided for introducing the material into the vessel to the desired level. Means for discharging the spent material from the chamber into a suitable receiver is also provided.

There is a closable outlet for the generated gas which leads from the upper portion of the chamber (which is not filled with fermentable material) to a suitable receiver.

The head is provided with projections of various kinds extending inwardly of the periphery of the chamber. Such projections may advantageously take the form of one or more perforated plates, one or more funnel or cone shaped members, etc. If the means for discharging the spent material is located around the periphery of the vessel, the funnel shaped elements are preferably slanted outwardly. On the other hand, if the means for discharging the spent material is centrally located, the funnel shaped elements are slanted inwardly.

The various projections are so located that, when the head is in its lowest position (the one closest to the vessel) at least some and preferably all are below the surface of the broth. When the head is in its uppermost position (the one remote from the vessel), at least some of the projections are above the surface of the material.

Thus, as the fermentation proceeds, the gas generated builds up a pressure within the slidable head. The head is forced to move upwards away from the vessel carrying with it the various projections. These projections both agitate the fermenting material and also break through the scum layer. In the preferred form of the device, the slanted upper surfaces of these projections urge the scum layer towards the meansfor discharging.

When the pressure has built up sufficiently and the head moved far enough upward, the gas outlet valve is opened and the gas is permitted to flow into a collector. The lowering of the pressure permits the head to fall of its own weight into its lower position. During this movement, the projections again pass through the scum layer and both break it up and agitate the fermenting mixture.

As a result of the foregoing, it can be seen that both agitation and scum discharge are obtained without the expenditure of any energy. The apparatus is entirely powered by the naturally generated gas.

It is to be understood that the term "projections" as used in this application is intended to be broadly construed. Clearly, the particular shape of the projections can be varied widely while still obtaining at least some of the improved resutls of the present invention. Any shape which would serve to break up the scum layer or agitate the material is useful in the present apparatus and process. Of course, the specifically mentioned shapes have been found to be particularly efficient.

The means for discharging the spent material is most advantageously of the overflow type. Such devices are energy efficient in that no pumps etc., are required. The gas carries the scum out of the chamber into the means for discharging and, from there, it is conveyed (preferably by gravity) to a suitable receiver. In the case of a centrally located discharge means, a stand pipe extending from the level to which the vessel is filled to the receiver (preferably located below) has been found advantageous. Similarly, in the case of a peripheral discharge means, an annular channel substantially surrounding the vessel has been found to operate quite satisfactorily. It is most preferred that this channel have a bottom which is slanted toward the discharge. Thus, the movement of the head and its projections urge the scum into the channel or central stand pipe, and gravity does the rest.

The materials of which the apparatus can be made are not particularly critical. Concrete, steel, plastics, or a combination thereof are all suitable. It is, of course, preferred that the materials used be resistant to the fermentable materials and the gas generated therefrom. It has been found that glass fiber reinforced plastics are quite satisfactory for free standing devices. Concrete has been found best for those which are sunk in the ground. Obviously, the fermentation portion of the device (the vessel) should be sufficiently insulated to minimize heat loss. As is recognized in the art, it is desirable to heat the vessel in order to promote the fermentation. A heating coil constructed of steel piping and located about 300 mm above the ground has been found effective. The heating can be obtained by the use of circulating hot water introduced at an appropriate temperature, for example, 80° C.

In addition to the foregoing, the effectiveness of the apparatus can be increased by rotation of the head as it moves in and out. This can be accomplished by using the force generated by the up and down movement of the head. Alternatively, suitable automatic apparatus can be provided. However, the latter course is somewhat less desirable since additional energy is required. It is, therefore, most advantageous to make the head and vessel circular in cross section to permit such rotational motion.

The fermentable material is introduced into the vessel by gravity. This merely requires that the tank holding the material be located above the vessel. Normal valves, etc. can be used and the material can be permitted to flow into the vessel at the desired rate. If this is not possible, a pump can be used.

In the accompanying drawings, constituting a part hereof and in which like reference characters indicate like parts;

FIG. 1 is a schematic representation of one embodiment of apparatus in accordance with the present invention;

FIG. 2 is a cross sectional view along line 1—1 of FIG. 1; and

Figure 3:
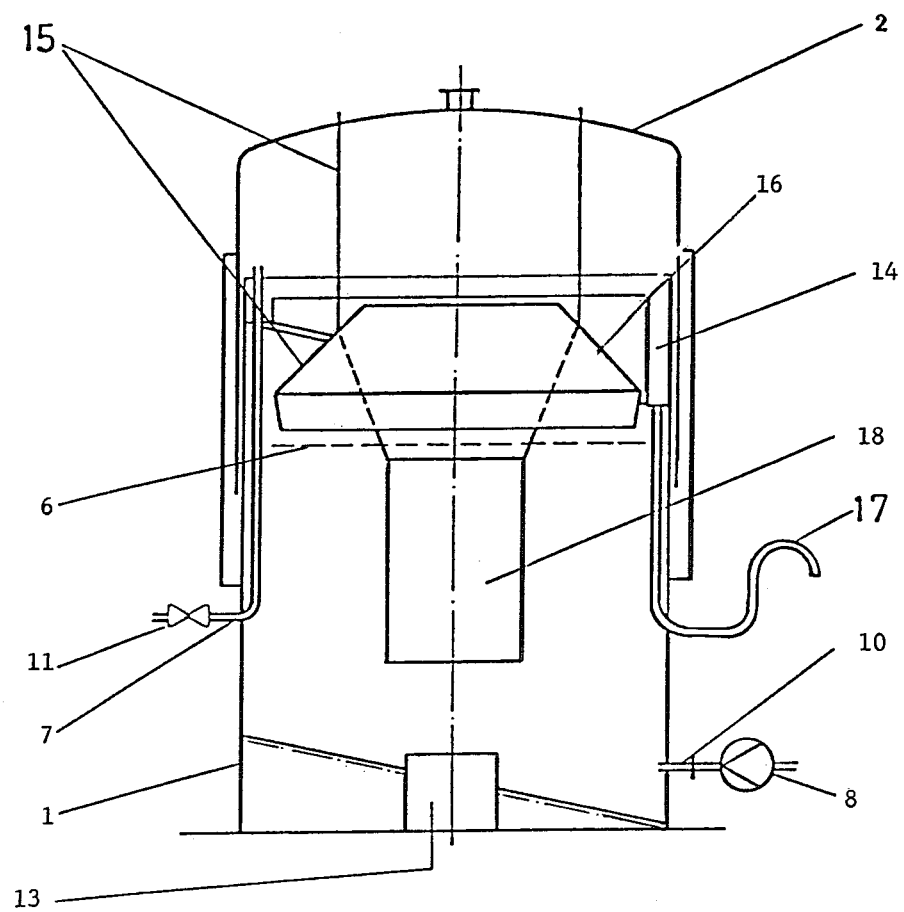
FIG. 3 is a schematic representation of a modified form of the present invention.

The apparatus comprises vessel 1 with head 2 slidably mounted thereon. Preferably, seal 19 is located therebetween in order to insure substantial gas tightness of the chamber.

Internal member 3 is affixed to head 2 and carries perforated plates 6 and funnel elements 16. Means for discharge 4 is located substantially on the axis of vessel 1 and head 2. Funnel elements 16 are slanted towards the center of the apparatus. Material pit 9 holds the supply of fermentable material. Pump 8 is between material pit 9 and inlet 10. Nearby, means for discharge 4 extends into receiver 5 which is provided with baffle 12 which aids in decanting the spent material.

In operation, pump 8 delivers the fermentable material through inlet 10 to vessel 1. The vessel is filled to the level of the upper end of means for discharge 4. The fermentation process is allowed to go forward and the gas generated moves upward through the liquid into the upper portion of head 2. This causes head 2 to move upward and funnel elements 16 to assume the position shown in FIG. 1. This movement not only breaks the scum layer, but also urges the scum into the means for discharge 4. In the most preferred form of the device, perforated plates 6 do not break the surface of the fermentation liquid. They are used primarily for agitation.

Valve 11 is opened and the gas flows through outlet 7 into a suitable collector (not shown). Head 2 then falls to its bottom position causing funnel elements 16 to break through the scum layer and, together with perforated plates 6, agitate the liquid.

In the embodiment shown in FIG. 3, the operation is very similar. In this Figure, some of the accessory apparatus has been omitted for clarity.

Vessel 1 is filled to the overflow level of annular channel 14 as shown. Head 2 acts in a manner analogous to the device of FIG. 1. However, the shape of the projections is different. In this embodiment, head 2 carries projections 15 which include plate 6, funnel element 16, and body 18. Vessel 1 is also provided with pedestal 13. Outlet pipe 17 leads from channel 14 to the receiver (not shown). The bottom of channel 14 is slanted towards outlet 17 so that the overflow scum will be removed by the force of gravity.

The operation of this device is analogous to that of the device of FIG. 1. However, funnel element 16 is slanted outwardly so that, as it rises through the scum layer, it urges the scum into channel 14, whence it flows through outlet pipe 17 into the receiver.

The angle of inclination of the bottom of channel 14 is preferably about 20 degrees to the horizontal. Similarly, the bottom of vessel 1 is also inclined to the horizontal at an angle of approximately 20 degrees in the preferred form of the device.

In operation, the pressure of the gas raises head 2 causing funnel element 16 to break through the scum layer from below and urge the scum radially outwardly into channel 14. The angle of the bottom of channel 14 causes the scum to flow through outlet pipe 17 into the receiver. When valve 11 is opened and the gas flows into the collector, head 2 returns to its bottom position wherein body 18 rests on pedestal 13. As in the previously described embodiment, funnel element 16 breaks through the scum on the way down and plate 6 aids in agitation.

The following examples are intended to illustrate the present invention.

EXAMPLE 1

The apparatus of the type illustrated in FIG. 1 comprises a vessel having a diameter of 4 m, a height of 4.3 m, and a volume of 50 m$^3$, and a head having a diameter of 3.8 m, a height of 2 m, and a total enclosed volume of 22 m$^3$. The apparatus is filled via inlet 10 using pump 8 with 50 m$^3$ of fermentable waste up to the level at which it flows over the upper end of means 4. Valve 11 is closed and the apparatus heated to 33° C., at which temperature anaerobic fermentation is begun. Scum, on the surface of the waste, and gas are produced, the gas giving rise to a pressure of about 30 mbar under the weight of the head. Evolution of the gas causes the head and its projections to rise until the position shown in FIG. 1 is reached. In this process, debris from the now broken scum is discharged into receiver 5 via means 4. Valve 11 is now opened. The gas streams out and is collected. The head and its projections and plates sink and the scum is broken up. The waste material is stirred up by the movement of the plates 6. The valve 11 is then closed and the process is started over again and is repeated as often as suitable.

In the preferred continuous operation of the process, 2 m$^3$ of fresh fermentable waste is fed into the apparatus daily and the same volume of fermented waste is discharged through the overflow. 50 to 70 m$^3$ of gas is obtained, measured at the pressure of the head given above.

EXAMPLE 2

Empty apparatus of the type shown in FIG. 3, comprising a vessel (diameter 4 m, height 4.3 m, volume 50 m$^3$) and head (diameter 3.8 m, height 2 m, total enclosed volume 22 m$^3$) was filled with 50 m$^3$ of fresh fermentable waste through inlet 10, using pump 8, until it flowed over into annular channel 14. Valve 11 is closed and the apparatus heated to 33° C. so that anaerobic fermentation began. Scum, on the surface of the waste, and gas were produced, the gas giving rise to a pressure of about 30 mbar under the weight of the head, its projections and body 18. The gas evolution caused the head to rise and, as a result, the debris of the broken scum is guided into annular channel 14 and thence through pipe 17. Valve 11 is now opened. The gas streams out and is collected. The head etc. sinks and the scum is broken up by projections 15. The whole waste material is stirred up by the plate 6 on each up and down movement of the head. Valve 11 is then closed again and the whole process recommences and is repeated as often as desired.

In the preferred continuous operation of the process, 2 m$^3$ of fresh fermentable waste is fed into the apparatus daily and the same volume of fermented waste discharged. 50 to 70 m$^3$ of gas is obtained, measured at the given pressure under the head.

While only a limited number of embodiments of the present invention have been specifically described, such changes as are apparent to the person of ordinary skill in the art may be made without departing from the spirit thereof.

For example, the projections may advantageously be helical in shape. In this form of the device, the rotational movement of the head relative to the vessel is particularly useful. The projections may also be in the form of one or more plungers as, for example, in piston pumps or airlift pumps.

The operation of the gas valve can be made automatic. Pressure actuated valves, such as are known in the art, can be used in place of a manual valve. Advantageously, the valve would be set to open at one pressure and close at a somewhat lower pressure. It is especially advantageous to couple the automatic valve with a constant feed. The fermentable material can be fed into the vessel at a steady rate. The spent material would be discharged at the same rate. In this way, the apparatus can operate unattended.

The head, while illustrated only in the hollow cylindrical form, may be a piston. It would operate in substantially the same way as the devices specifically described.

Since these and other changes may be made by those of ordinary skill, the present invention is to be broadly construed and not to be limited except by the character of the claims appended hereto.

We claim:

1. Apparatus for the recovery of gas evolved from fermentation, comprising: a vessel for receiving fermentable material; a head mounted on said vessel to define a substantially gas-tight chamber therebetween, said head being movable toward and away from said vessel; means for discharging the fermentable material from said chamber into a receiver after fermentation of the material; means for introducing the fermentable material into said vessel to a predetermined height therein; and a closable outlet for the gas evolved from fermentation of the material, said outlet communicating with the chamber at a location above said predetermined height to which the fermentable material is introduced; said head having at least one projection movable therewith and disposed at least partially in said chamber, and at least a portion of said projection extending below said predetermined height of the fermentable material when said head is at its closest position relative to the vessel and above said predetermined height when the head is at its furthest position relative to the vessel; said projection being slanted toward said discharging means such that movement of the head toward and away from said vessel urges the fermentable material toward said discharging means.

2. Apparatus according to claim 1 wherein all of said projection is disposed above said predetermined height when the head is at its furthest position relative to the vessel.

3. Apparatus according to claim 1 wherein said projection is affixed to the head.

4. Apparatus according to claim 1 wherein said projection includes a perforated plate in said chamber.

5. Apparatus according to claim 1 wherein said discharging means is disposed substantially at said predetermined height.

6. Apparatus according to claim 1 wherein said discharging means is located centrally in said chamber.

7. Apparatus according to claim 1 wherein said discharging means is located peripherally of said chamber.

8. Apparatus according to claim 1 wherein said discharging means comprises an annular channel.

9. Apparatus according to claim 1 including a substantially gas-tight seal between said vessel and said head.

10. Apparatus according to claim 1 wherein said vessel has a base which is slanted toward the receiver.

11. A process for the fermentation of fermentable material comprising:
    introducing the fermentable material into the vessel of claim 1;
    closing the gas outlet; and
    allowing the fermentation to take place whereby gas is generated, the gas causing the head to move away from the vessel such that said at least one projection of the head breaks a scum layer on top of the fermentable material and thereby urges the scum toward said discharging means.

12. Apparatus for the recovery of gas evolved from fermentation, comprising: a vessel for receiving fermentable material; a head mounted on said vessel to define a substantially gas-tight chamber therebetween, said head being movable toward and away from said vessel; means for discharging the fermentable material from said chamber into a receiver after fermentation of the material; means for introducing the fermentable material into said vessel to a predetermined height therein; and a closable outlet for the gas evolved from fermentation of the material, said outlet communicating with the chamber at a location above said predetermined height to which the fermentable material is introduced; said head having at least one projection movable therewith and disposed at least partially in said chamber, and at least a portion of said projection extending below said predetermined height of the fermentable material when said head is at its closest position relative to the vessel and above said predetermined height when the head is at its furthest position relative to the vessel; said projection including at least one funnel-shaped element.

13. Apparatus according to claim 12 wherein said funnel-shaped element tapers in a direction away from the periphery of said chamber.

14. Apparatus for the recovery of gas evolved from fermentation, comprising: a vessel for receiving fermentable material; a head mounted on said vessel to define a substantially gas-tight chamber therebetween, said head being movable toward and away from said vessel; means for discharging the fermentable material from said chamber into a receiver after fermentation of the material; means for introducing the fermentable material into said vessel to a predetermined height therein; and a closable outlet for the gas evolved from fermentation of the material, said outlet communicating with the chamber at a location above said predetermined height to which the fermentable material is introduced; said head having at least one projection movable therewith and disposed at least partially in said chamber, and at least a portion of said projection extending below said predetermined height of the fermentable material when said head is at its closest position relative to the vessel and above said predetermined height when the head is at its furthest position relative to the vessel; said projection comprising at least one helical element.

* * * * *